(12) United States Patent
Sundman et al.

(10) Patent No.: US 6,205,230 B1
(45) Date of Patent: Mar. 20, 2001

(54) OPTICAL CONTOUR DIGITIZER

(75) Inventors: Arjen Sundman, Santa Cruz; James T. Walker, Palo Alto, both of CA (US)

(73) Assignee: Amfit, Inc., Santa Clara, CA (US)

( * ) Notice: Subject to any disclaimer, the term of this patent is extended or adjusted under 35 U.S.C. 154(b) by 0 days.

(21) Appl. No.: 09/191,746

(22) Filed: Nov. 12, 1998

(51) Int. Cl.[7] ........................................... G06K 9/00
(52) U.S. Cl. ............................................... 382/100
(58) Field of Search .................... 382/106, 108, 382/154, 209, 286, 287, 312, 316; 356/376, 377; 348/77, 100

(56) References Cited

U.S. PATENT DOCUMENTS

| | | | |
|---|---|---|---|
| 4,858,621 | 8/1989 | Franks | 600/592 |
| 5,128,880 | 7/1992 | White | 382/165 |
| 5,237,520 | 8/1993 | White | 382/154 |

*Primary Examiner*—Andrew W. Johns
*Assistant Examiner*—Shervin Nakhjavon
(74) *Attorney, Agent, or Firm*—Ohlandt, Greeley, Ruggiero & Perle, L.L.P.

(57) ABSTRACT

The invention includes both a method and apparatus for measuring the shape of a surface of an object, such as a human foot. The apparatus includes a support for holding a compliant sheet of known color and retro-reflectivity. The compliant sheet conforms to the shape of the undersurface of the foot. A scanner scans a light beam along the undersurface of the compliant sheet from a vantage point that is below the compliant sheet. A sensor detects reflected light from the undersurface of the compliant sheet and feeds corresponding light value signals to a processor. The processor analyzes the signals and determines distance values to portions of the compliant sheet. The distance values enable a contour to be derived that is representative of the undersurface of the foot.

22 Claims, 9 Drawing Sheets

OPTICAL CONTOUR DIGITIZER

FIELD OF THE INVENTION

This invention relates in general to the precise measurement of a contoured surface and, more specifically, to measurements of the contour of the undersurface of the foot.

BACKGROUND OF THE INVENTION

Every foot is different and all require proper fitting of footwear in order to maintain good foot health. Measurement of the foot has long been done using length and width measurements. Those measurements yield a fair characterization of the general attributes of the foot, but fail to address the unique shape of the undersurface of the foot.

A number of prior art devices have, with varying degrees of success, measured the undersurface of the foot. Optical scanners that use a laser line optic that is projected onto the underside of a foot and a video camera that records the modified location of the reflected line, produce accurate contours. This technique only works well in a non-weightbearing circumstance. The reason is that the foot increases in length by approximately one size (the width also expands) when weight is applied. Measurement of the foot using such a scanner in a non-weight bearing arrangement will result in a data set that does not allow for this natural expansion of the foot in gait.

U.S. Pat. No. 5,689,446 to Sundman et al. and assigned to the same Assignee as this Application, describes a foot contour digitizer wherein a foot is first placed on an array of gauge pins which are in turn deflected to reflect the contour of the underside of the foot. The gauge pins are urged upward by a diaphragm that is moved by air pressure. The deflected gauge pins are then scanned to derive a data set that defines the foot contour.

While the aforementioned measurement device has the advantage of supporting the foot while measurement takes place, the device is inherently expensive, with its hundreds of gauge pins. Details of the gauge pin structure are found in U.S. Pat. No. 4,876,758 to Rollof and assigned to the same Assignee as is this Application.

Franks, in U.S. Pat. No. 4,858,621 discloses a foot pressure measurement system wherein a transparent flat surface is edge-lighted and supports a pliable material on which is placed a foot to be imaged. When the foot applies pressure to the pliable material, an increase in light intensity results in proportion to the pressure, which is sensed by a scanner. The light intensity variations are converted to foot pressure data.

If one places a foot against a transparent flat surface and uses a laser scanner to measure the contour of the undersurface of the foot, the resultant image reflects a contour with large unnatural flat areas of the foot where the foot contacts the transparent surface. Such a device is described in U.S. Pat. Nos. 5,128,880 and 5,237,520 to White.

White discloses a scanner that is similar to a flat plate document scanner, where the undersurface of the foot is imaged in color and the image data is processed to produce elevation data. The White device uses the principle that surfaces that are further away from the contact surface of the scanner will appear darker in the image data.

A problem with the White device is that there is no way to accurately determine the exact distance from the support surface of portions of the foot, using the data which results from the scanned foot image intensities. The variables which act to vary the intensity data include: variations in skin tone and color, ambient light, whether the subject foot is wearing a sock, and the amount of weight applied to the foot. Further, the lowest foot surfaces are whiter in relation to other areas of the foot due to reduced blood flow. Nevertheless, the White structure does exhibit the advantages of: use of an inexpensive flat bed scanner; providing an accurate perimeter of the foot; and providing enough information to characterize certain portions of the foot, e.g. high, low, or sheet arch height.

Even allowing for the variables discussed above, the intensity information acquired from an optical scanner is the sum of three components:

1. The position of the light source relative to the subject surface.
2. The incident angle of light projected onto the subject surface.
3. The distance of the subject surface from the reference surface.

To measure the contour of an object, such as a human foot, the above three components must be taken into consideration. Other variables must be eliminated, or allowed for, to derive accurate elevation data.

Accordingly, it is an object of the invention to provide an improved system for characterizing the undersurface of a foot.

It is another object of the invention to provide an improved system for characterizing the undersurface of a foot that provides consistent intensity data and enables accurate contour data to be derived.

It is a further object of the invention to provide an improved system for characterizing the undersurface of a foot that provides highly accurate foot contour data and enables the production of custom foot supports in accordance therewith.

SUMMARY OF THE INVENTION

The invention includes both a method and apparatus for measuring the shape of a surface of an object, such as a human foot. The apparatus includes a support for holding a compliant sheet of known color and retro-reflectivity. The compliant sheet conforms to the shape of the undersurface of the foot. A scanner scans a light beam along the undersurface of the compliant sheet from a vantage point that is below the compliant sheet. A sensor detects reflected light values from the undersurface of the compliant sheet and feeds corresponding signals to a processor. The processor analyzes the signals and determines distance values to portions of the compliant sheet. The distance values enable a contour to be derived that is representative of the undersurface of the foot.

DETAILED DESCRIPTION OF THE INVENTION

Figure 1:
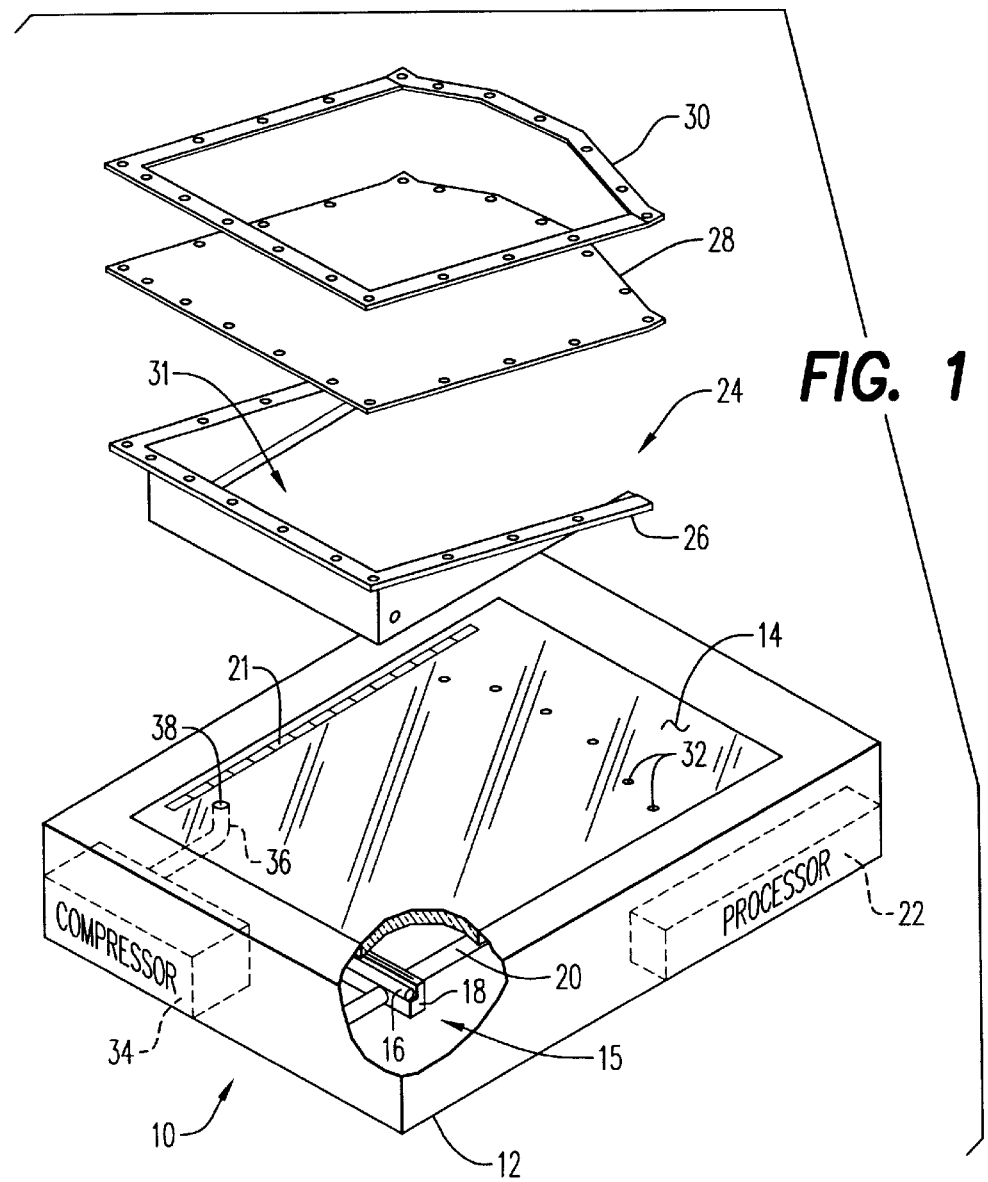
FIG. 1 is an exploded perspective view of a preferred embodiment of an apparatus that incorporates the invention.

Referring to FIG. 1, an optical scanner 10 is configured much the same as a flat plate document scanner. In that regard, optical scanner 10 includes a housing 12 and an upper, transparent plate 14 which may be either glass or a polymer/acrylic material. An optical scan structure 15 is positioned within housing 12 and includes a light source 16 and a linear detector array 18, both of which are mounted for movement on a pair of rails 20 (only one rail is shown). A measure bar 21 is positioned on transparent plate 14 and is used to obtain a measure of the length of a foot being imaged. Motor means are present within housing 12 (not shown) and enable the optical scan structure 15 to move beneath transparent plate 14 in substantially the same manner as in prior art document scanners.

As indicated above, the position of the light source is an important consideration in achieving reliable elevation information. First, the light source must provide uniform illumunation from the camera's viewpoint. Most commercially available flatbed document scanners use a light source 16 on one or the other side of an active scanning opening. This yields a light source that is suited to the purpose for which the scanner was designed (namely scanning a flat sheet of paper a known distance from the active scanner opening), but yields a light source that will unevenly light an uneven surface.

Figure 2A:
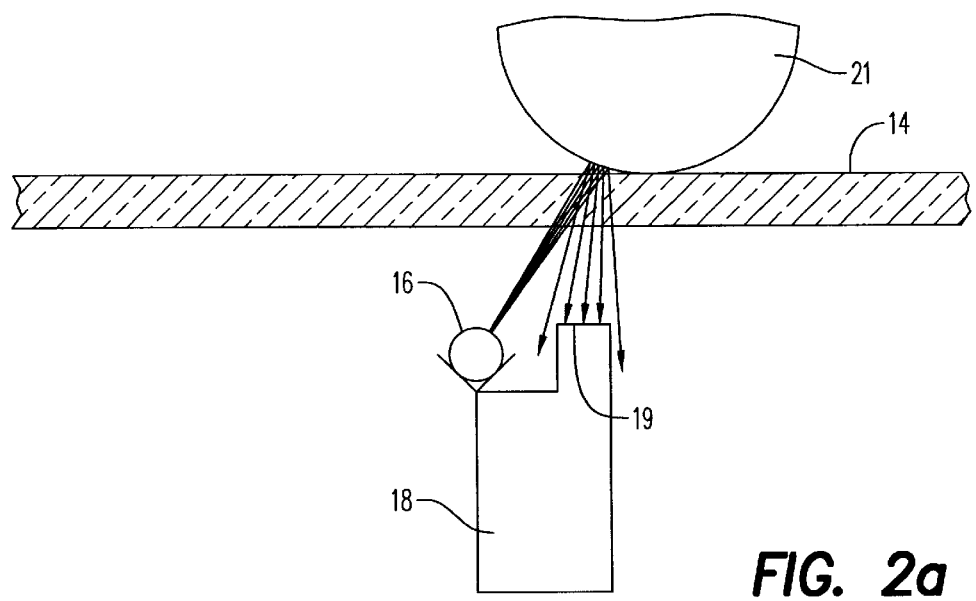
FIG. 2a is an expanded schematic view of a scan mechanism.

FIG. 2a shows a measured surface 21 that is more perpendicular to the light source's emitted light and is more efficient at reflecting that light towards the scanner's active scanning element opening 19. This is aided by addition of a "reflex light source", as shown in FIG. 2b.

Figure 2B:
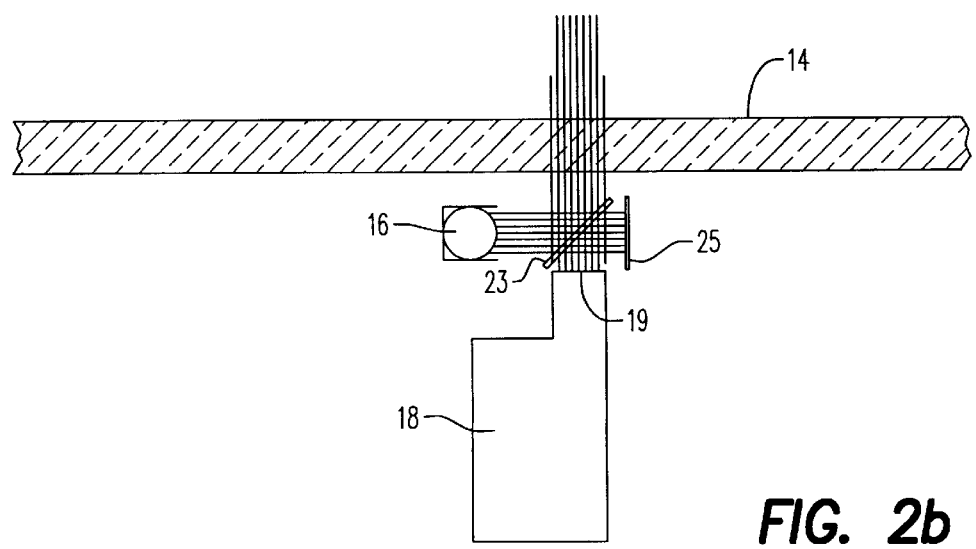
FIG. 2b is an expanded view of a first preferred scan mechanism for use with the invention.

The arrangement of FIG. 2b reflects the source light off of a 50% reflective mirror 23 located directly in the active scanning area of the scanner. Mirror 23 reflects 50% of the source's light directly at surface 21. Light not reflected by mirror 23 is sent to light sink 25, to prevent stray light from interfering with the scanning. The embodiment of FIG. 2b makes the apparent light location the same as the scanner's location and yields a near perfect lighting configuration.

Figure 2C:
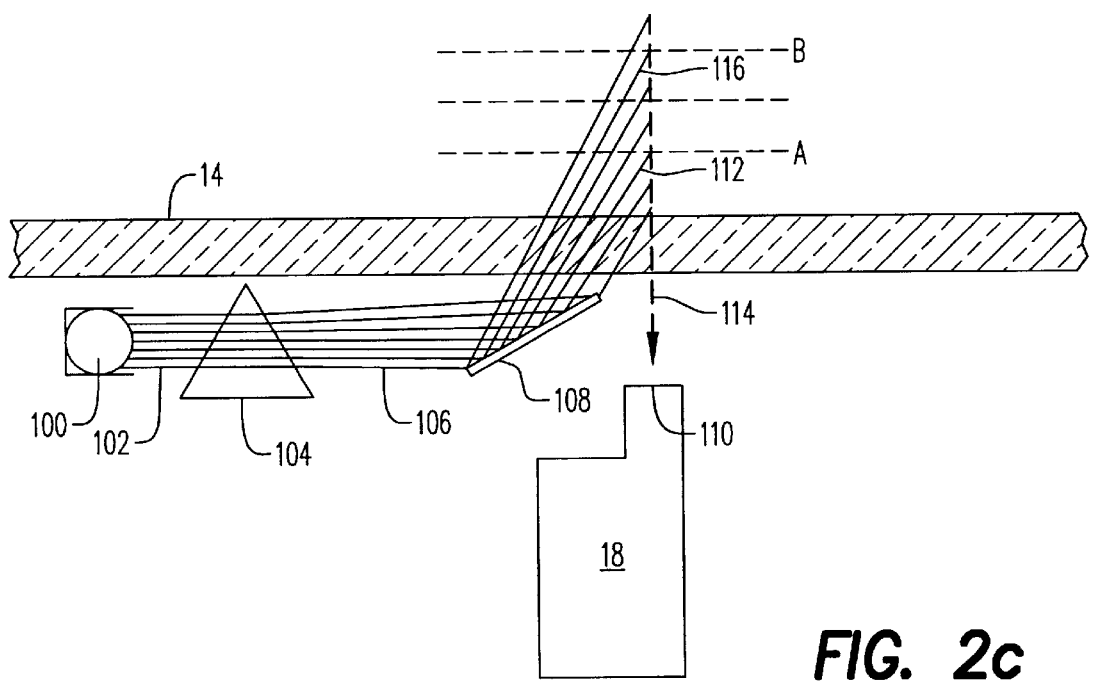
FIG. 2c is an expanded view of a second preferred scan mechanism for use with the invention.

A further scanner embodiment is shown in FIG. 2c and includes a collimated light source 100 whose output beam 102 is passed through a prism 104 which converts light beam 102 into a beam 106 comprising a rainbow of colors. Rainbow beam 106 is then reflected upwardly by mirror 108 onto the body being imaged. Any contoured item in the projection path of rainbow beam 106 will reflect a color back to color detector 110 that is a function of the distance of the body from reference surface 14. For instance, if the reflecting surface is positioned at level A, color 112 is reflected along axis 114 to detector 110. If the reflecting surface is positioned at level B, color 116 is reflected along axis 114 to detector 110, etc. So long as the field of view of detector 110 is restricted to the immediate region of axis 114, the other reflected colors are ignored.

As an alternative design, a strip of differing color film and a lens can be substituted for prism 104.

Returning to FIG. 1, a processor 22 receives signals from linear detector array 18 that are indicative of intensities of reflected light from a surface being imaged. The operations of processor 22 will be considered in detail below.

A slanted support structure 24 is positioned on an uppermost surface of housing 12 and is affixed thereto. A flange 26 extends about the outer periphery of support structure 24 and mates with the outer edges of a compliant sheet 28 that rest thereupon. Compliant sheet 28 is preferably a flexible sheet of known color and retro-reflectivity. A surface that is retro-reflective has the property that it sends incident light rays back to the direction from where they came. By incorporating a retro-reflective surface, the slope of the reference surface relative to the reference surface has little impact in gray scale image data at slope angles of less than 30 degrees. At slope angles in excess of 30 degrees, the flexible sheet is less efficient at reflection. The reduced efficiency is compensated for in software post-processing.

Figure 3:
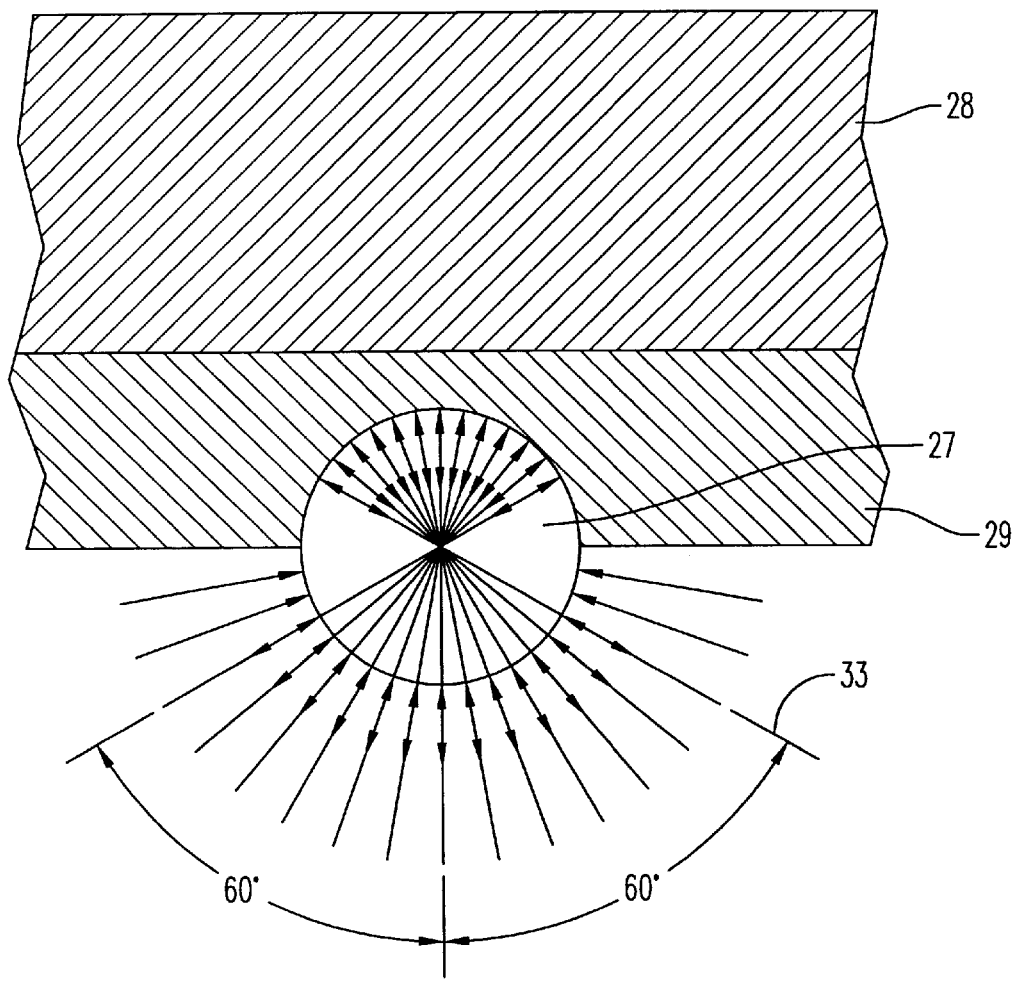
FIG. 3 illustrates a retro-reflective bead on a compliant sheet.

A preferred method for achieving retro-reflectivity is by embedding glass microspheres 27 into the undersurface of compliant sheet 28 (see FIG. 3). Microspheres 27 are adhered to compliant sheet 28 using an elastic coating 29. Glass microspheres 27 are slighty mirrored and have an index of refraction of approximately 1.5. Ambient incident light 33 that enters a microsphere 27 from off axis angles of over about 60 degrees is rejected and the rest is accepted. The accepted light that enters a microsphere 27 bounces off an interior reflective surface and is emitted at the same angle from whence it came.

In an alternative embodiment, the undersurface of compliant sheet 28 need not be continuously coated with microspheres 27 and embedding ink 29. They need only be applied periodically (as in a dot pattern for instance). This will allow compliant sheet 28 greater flexibility than a continuous coating, as well as offering greater potential lifetime.

In a further embodiment, the microspheres can be embedded directly into compliant sheet 28. This is accomplished during manufacture of the complaint sheet. The method of embedding can be by heating to slightly melt the surface of compliant sheet 28 and thereafter embedding microspheres 27 therein.

Regardless of the method employed, for optimum retro-reflectivity, microspheres 27 should be embedded to approximately ½ of their diameter, and the sheet into which they are embedded should have a uniform color or reflectivity.

In yet another embodiment, the compliant sheet need not have embedded microspheres but should preferably have a highly reflective coloration. Software processing is then needed to compensate for non-linearities in the image data intensity vs. elevation.

Returning to FIG. 1, a frame 30 sandwiches and seals the outer edges of compliant sheet 28 against flange 26. A series of holes 32 are present in transparent plate 14 and enable the attachment of frame 30, and an underlying edge of compliant sheet 28 directly to transparent plate 14.

When frame 30, compliant sheet 28 and support structure 24 are assembled on the upper surface of housing 12, an air-tight volume 31 is created between the lower surface of compliant sheet 28 and the upper surface of transparent plate 14. An air compressor 34 is positioned within housing 12 and is coupled, via a tube 36, to an outlet 38 which leads into air-tight volume 31. Air compressor 34 is controlled to maintain a level of pressure within volume 31 such that when a foot, or other object, is placed upon compliant sheet 28, compliant sheet 28 remains sufficiently flexible to form around the foot/object but is maintained just out of contact with transparent plate 14.

Figure 4:
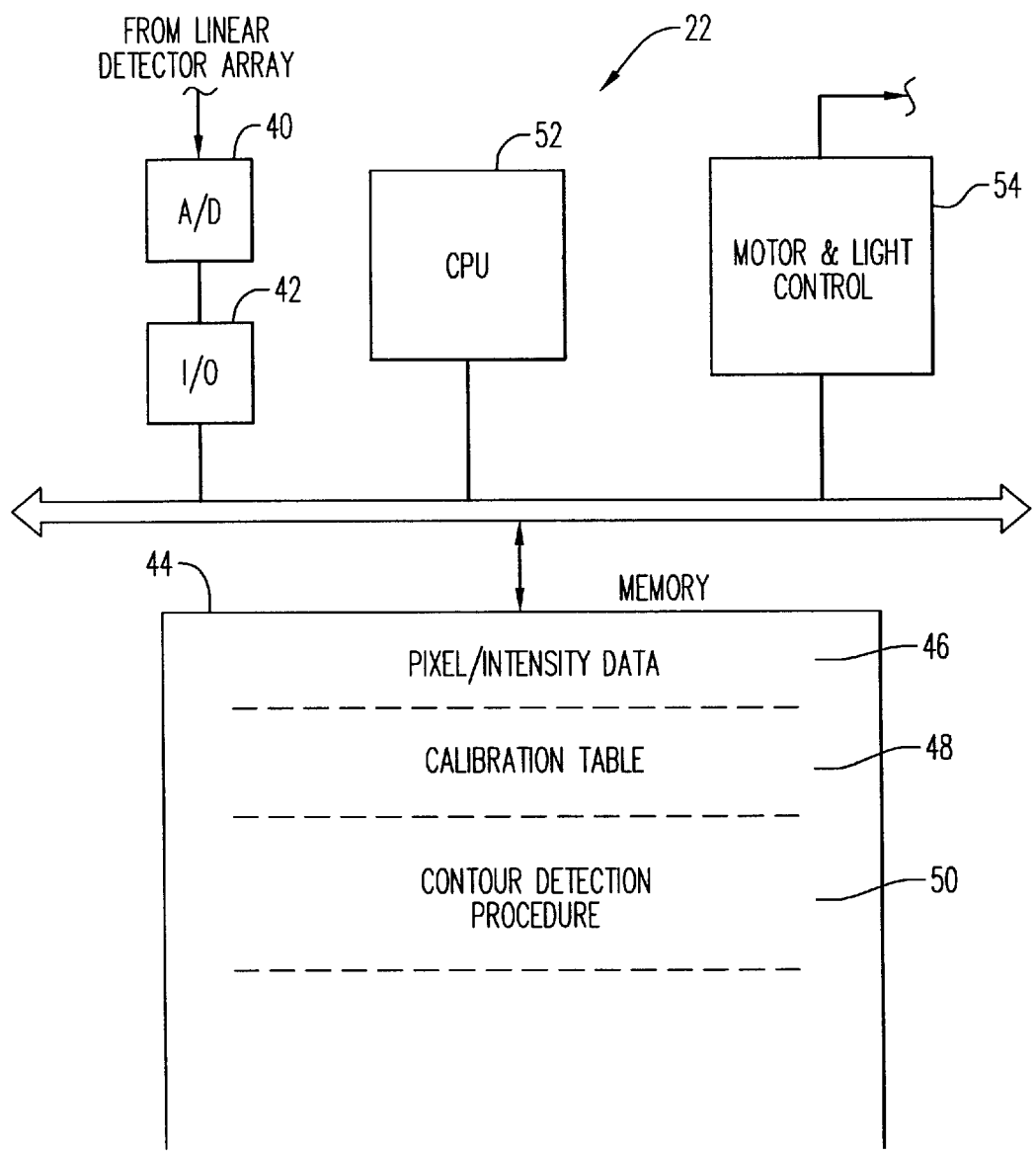
FIG. 4 is a block diagram of elements of the processor shown in FIG. 1.

Turning now to FIG. 4, the block diagram shown therein illustrates the major components of processor 22. Signals from detector array 18 are fed through an analog to digital (A/D) converter 40 and an input/output module 42 and are stored in a memory 44 in the form of pixel/intensity data 46. Also stored within memory 44 is a calibration table 48 which equates intensity levels to distances from a reference or datum surface (e.g., transparent plate 14 or the flat surface defined by a plane resident on flange 26, FIG. 1).

Memory 44 further includes a contour detection procedure 50 which enables the derivation of contour values from the pixel/intensity data 46 derived during a scan action of optical scan structure 15. In the latter regard, contour detection procedure 50, in combination with central processing unit (CPU) 52, operates upon the pixel intensity data 46 and utilizes the distance entries in calibration table 48 to arrive at the contour data. CPU 52 also issues signals to a motor/light control module 54 which, in turn, controls the operation of light source 16 and the motor which moves optical scan structure 15 beneath transparent plate 14.

Referring to FIGS. 5a–5d, the method of the invention will be described. FIG. 3A illustrates a cutaway side view of optical scanner 10, prior to volume 31 having been pressurized by operation of air compressor 34. At this stage, compliant sheet 28 is uninflated and droops into volume 31 of support structure 24. As shown in FIG. 3B, when air compressor 34 is energized by a signal from CPU 52, airflow into the volume 31 causes compliant sheet 28 to extend upwardly as a result of a pressure build-up in volume 31.

Figure 5A:
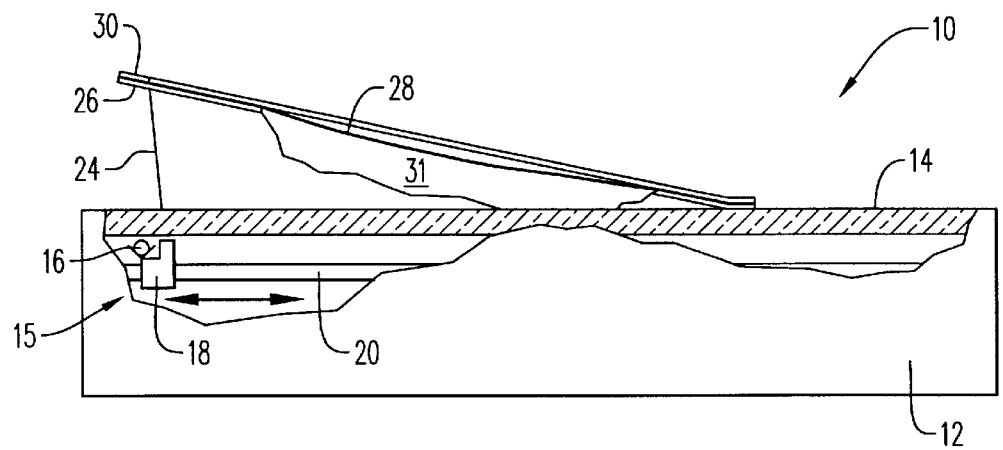
FIGS. 5a–5d illustrate the operation of the apparatus of FIG. 1, during the process of acquiring contour data of the underside of a foot.
Figure 5B:
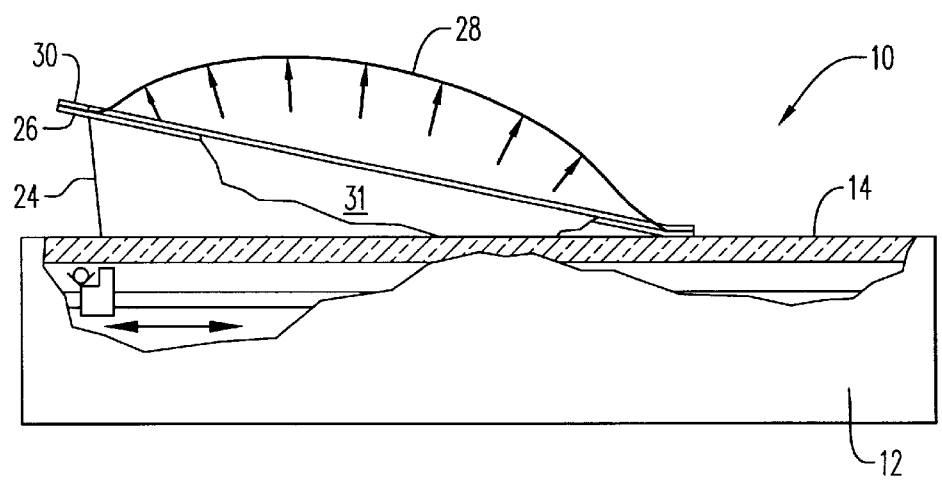
Figure 5C:
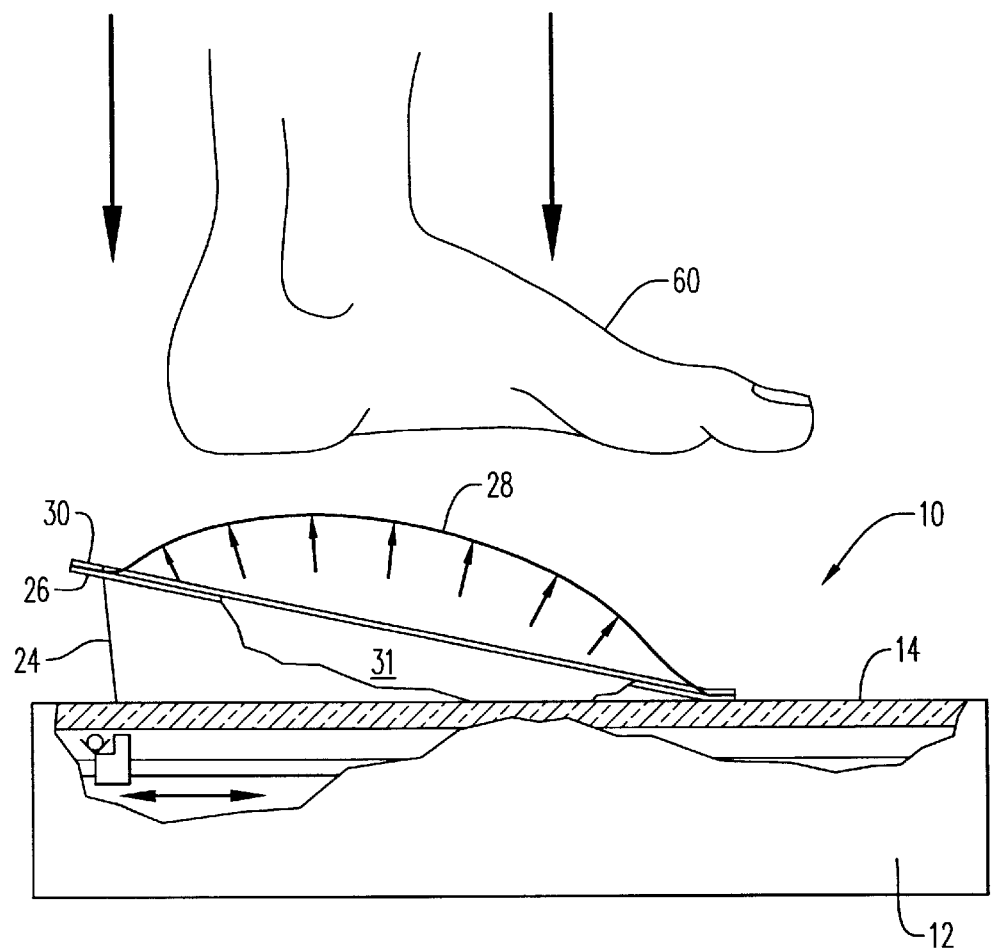
Figure 5D:
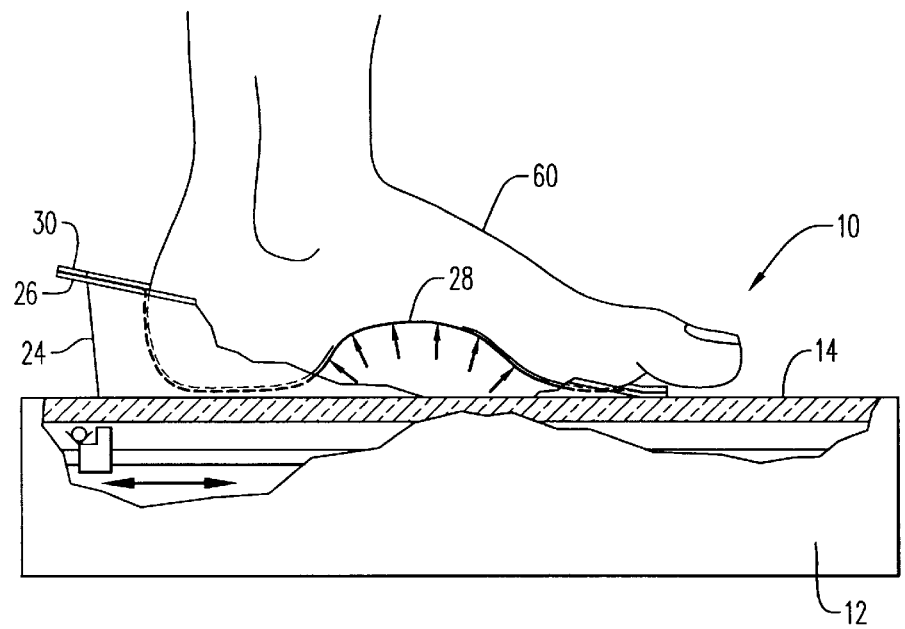

As shown in FIG. 5c, a foot 60 is about to be placed on compliant sheet 28. Note that both the heel and the arch of foot 60 are positioned directly above the uppermost regions of support structure 24. Thus, when foot 60 is in full contact with compliant sheet 28 (as shown in FIG. 5d) compliant sheet 28 molds itself to the shape of the arch and heel in an enveloping fashion. The air pressure within volume 31 is maintained at a level that allows the portion of compliant sheet 28 that is immediately below the heel of foot 60 to either just touch or, preferably, be just offset from the upper surface of transparent plate 14.

Accordingly, compliant sheet 28 molds itself to the bottommost surface of foot 60 and provides a uniformly colored surface for subsequent scanning. Note that the arrangement shown in FIG. 5d enables the imaging of the heel and arch (behind the metatarsels) as those are the regions of a foot whose dimensions must be known in order to enable the configuration of an orthotic support structure therefor.

Once foot 60 is in place, as shown in FIG. 5d, processor 22 is instructed to commence a scan action. Accordingly, CPU 52 issues a signal to motor/light control module 54 to commence movement of optical scan structure 15 (FIG. 1). Accordingly, light source 16 is energized and projects a beam upwardly onto the undersurface of compliant sheet 28. The reflections from compliant sheet 28 are sensed by linear detector array 18, causing analog light intensity signals to be fed to A/D converter 40, which converts those signals to digital intensity values. Those digital intensity values are then stored in pixel/intensity data region 46 of memory 44.

Once a complete scan has been accomplished, contour detection procedure 50 causes each intensity value to be used to address calibration table 48 which, in turn, returns a distance value that is indicative of the distance of the respective pixel position from the datum surface. Once those distance values are accumulated, an accurate contour of the underside of foot 60 has been created which can later be used in constructing an orthotic foot support. For instance, the contour values can be used to determine the amount of a conformable material to be injected into a mold to create an orthotic or an insole that matches the underside of the foot. Further, the contour values can be used to control the machining of a blank to produce an orthotic matched to the underside of a user's foot.

The light intensity values derived during a scan exhibit a progressively darker value as the distance increases between the scanned surface of compliant sheet 28 and transparent plate 14. Since the slope of support structure 24 is known, and the change in elevation between successive scan lines is also known, the elevation for any light intensity level observed at any given point can be derived. It is preferred that calibration table 48 be derived initially to enable a table lookup operation to be performed when converting from intensity values to distance values. In addition to the contour data, a sensing of the marking increments on measuring bar 21 during the scanning action enables a length dimension of the foot to be acquired.

To calibrate the system, a flat plate (not shown) is placed at an angle relative to the reference surface (e.g., transparent plate 14) and air is introduced into interior 31 of support structure 24. Compliant sheet 28 is thus forced against the undersurface of the flat plate. Thereafter, a gray scale scan is performed of the underside of compliant sheet 28. The digitized image is processed and saved.

The area recorded with the slanted flat plane in view exhibits a progressively darker image as the plane moves further away from the reference surface, (or in the event no reference surface is used), the scanning plane. Since the size of the flat calibration plane is known and the angle at which it was placed relative to the reference surface or scanning plane is known, the elevation for any given intensity can be derived. Those elevation distances are then stored in calibration table 48, which correlates the distance values to the respective light intensity values which gave rise thereto. Then, when a foot is scanned, the resulting intensity values derived from the underside of compliant sheet 28 are used to address the calibration table 28, enabling read-out of the corresponding distance values.

There are other methods that can be used to calibrate the system. Instead of a flat plane, a sphere can be used with a known radius. The sphere is placed against compliant sheet 28 such that it is tangent to the reference surface or the scanning plane. Air is then introduced into support structure 24 and the compliant sheet 28 is caused to assume the shape of the sphere. Compliant sheet 28 is scanned and the resulting image analyzed. Each elevation represented by an observed intensity can be readily derived when the radius of the sphere is known.

Once contour image data is acquired, contour detection procedure 50 performs image processing actions to capture the portion of the image directly related to the foot contour. More particularly, contour detection procedure 50 finds the active areas of the foot in the image by sensing edge pixels which encompass the contour image (e.g., by looking for pixels which, after a run of constant intensity pixels, commence a change of intensity—indicating a boundary between a non-stressed portion of compliant sheet 28 and a stressed portion thereof). The image is then trimmed so that a portion behind the heel is eliminated.

Thereafter, the heel area is centered in the image area and it is then rotated so that the forefoot is also in the middle of the image area. Next, any image areas outside of the image boundary are trimmed. Thereafter, the pixel intensity values within the now-captured foot contour region are converted to height values by referring the pixel intensity values to calibration table 48 and reading out the respective height data.

Figure 6:
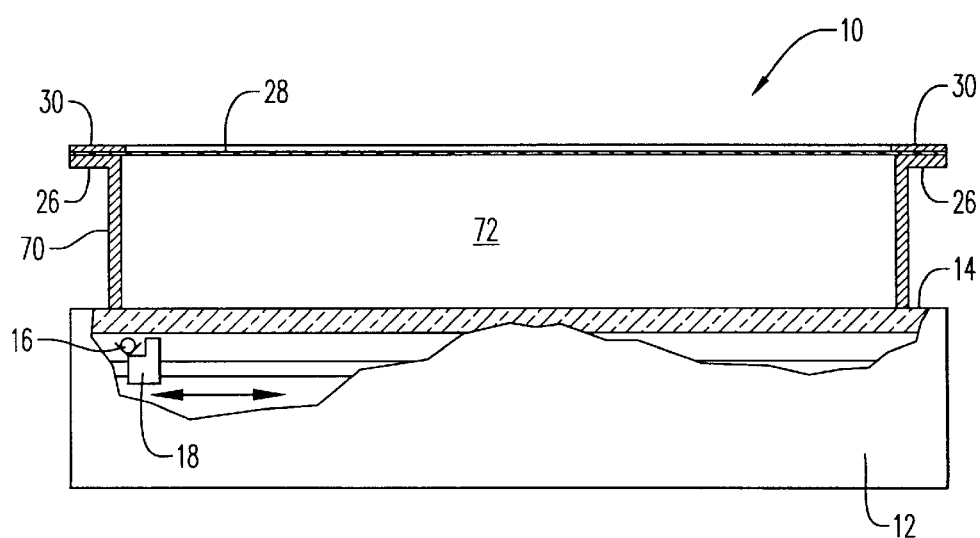
FIG. 6 is a schematic side view of a further embodiment of the invention.

Turning now to FIG. 6, a further embodiment of the invention is illustrated wherein support structure 70 is arranged so that compliant sheet 28 is held parallel to transparent plate 14. Accordingly, when a foot is thereafter placed on compliant sheet 28, the sheet stretches and assumes the shape of the foot surface. An air supply is optional in this embodiment, but is preferred so as to enable pressurization of volume 72 so as to enable control of of the amount of deflection of compliant sheet 28.

Figure 7:
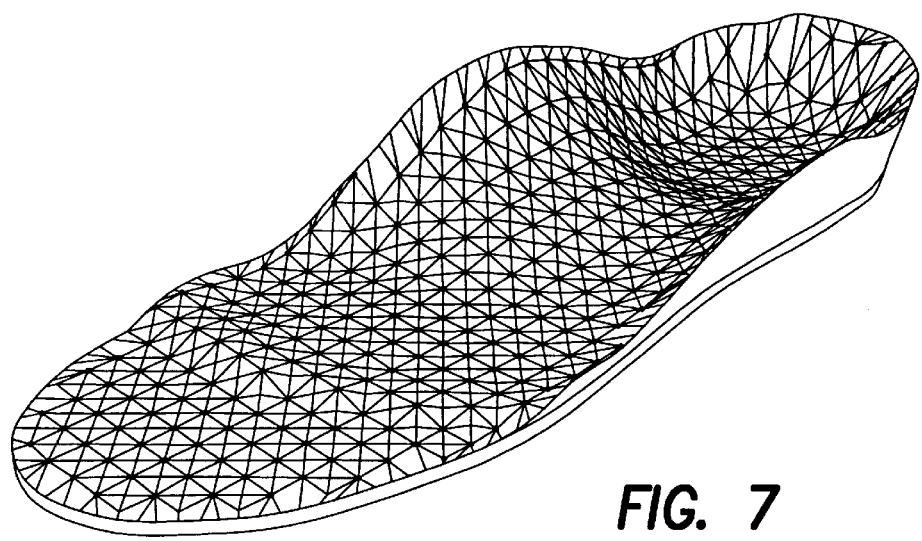
FIG. 7 is a perspective view of an insole that is constructed using data achieved through operation of the invention.
Figure 8:
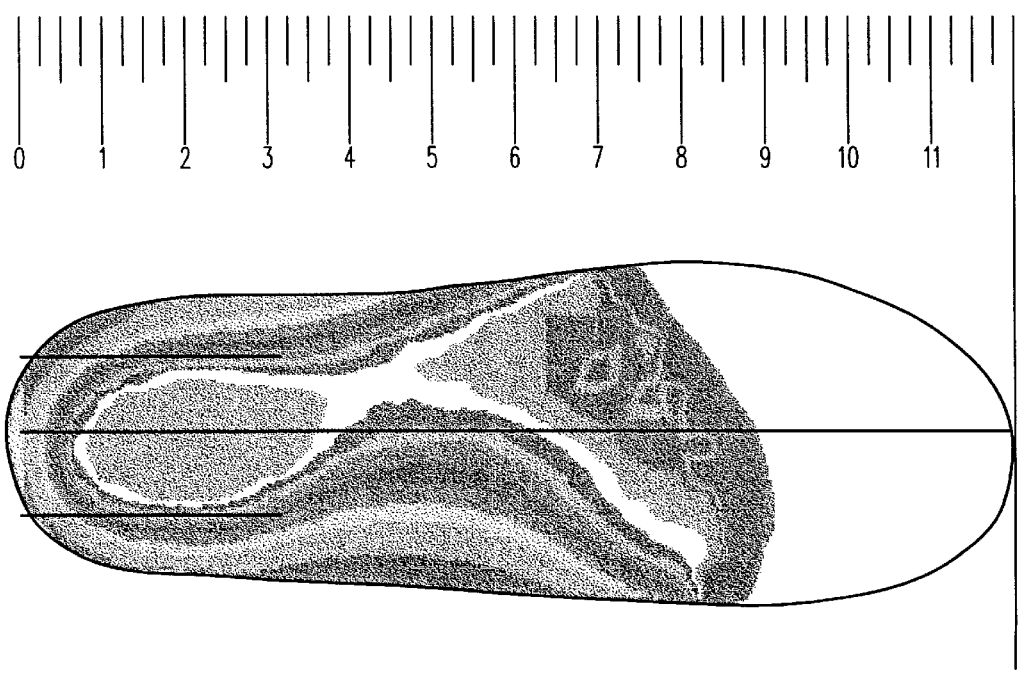
FIG. 8 is a contour illustration of the underside of a foot using data acquired through operation of the invention

FIG. 7 illustrates a three dimensional view of an insole that is configured through use of the foot contour data derived as described above. FIG. 8 illustrates a contour image that is constructed from the foot contour data. It is preferred that the individual contours be shown in different colors to enable the user to better visualize foot surface differences.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A method of measuring the shape of an undersurface of an object, the method comprising the steps of:
    a) placing a surface of the object against a compliant sheet so as to cause said compliant sheet to conform to a shape of the surface of the object;
    b) scanning the undersurface of the compliant sheet with a light beam, from a vantage point that is below the compliant sheet;
    c) sensing reflected light intensities from said undersurface of the compliant sheet during said scanning; and
    d) determining distance values to portions of the compliant sheet from measured data derived from said reflected light intensities, said distance values enabling a contour to be derived of said surface of said object.

2. The method as recited in claim 1, further comprising the steps of:
    i) prior to placement of said object, scanning the undersurface of the compliant sheet with a light beam, from a vantage point that is below the compliant sheet;
    ii) sensing reflected light intensities from said undersurface of the compliant sheet during said scanning; and
    iii) determining reference distance values to portions of the compliant sheet using said data derived from said reflected light; and
    wherein step d) employs said reference distance values and measured data to determine positions of said compliant sheet.

3. The method as recited in claim 1, wherein step b) is accomplished by moving a light beam along said undersurface of said compliant sheet, said light beam projected against said compliant sheet from beneath.

4. The method as recited in claim 1, wherein step b) is accomplished by moving a light beam evidencing multiple separate colors along said undersurface of said compliant sheet, and step c) senses a particular color of reflected light in accordance with a distance of said compliant sheet from a detector.

5. The method as recited in claim 1, wherein said object is a human foot.

6. The method as recited in claim 5, comprising the further step of:
    determining from said contour, an amount of material to inject into a form to provide an insole for support of the foot.

7. The method as recited in claim 5, comprising the further step of:
    determining from said contour, an amount of material to inject into a form to provide an orthotic for support of the foot.

8. The method as recited in claim 5, comprising the further step of:
    determining from said contour, an amount of material to be machined from a blank to provide an insole or an othotic for support of the foot.

9. The method as recited in claim 5, comprising the further step of:
    determining from said contour, data to enable display of a multi-contour representation of the underside of said foot.

10. The method as recited in claim 5, comprising the further step of:
    determining from said contour, data to enable display of a three dimensional view of an insole for support of the foot.

11. Apparatus for measuring a shape of a surface of an object, said apparatus comprising:
    a) support means for holding a compliant sheet, said compliant sheet responsive to placement of said surface of said object thereagainst to conform to a shape of said surface;
    b) scanning means for scanning a light beam along an undersurface of the compliant sheet, said scanning means oriented to project said light beam from a vantage point that is below the undersurface of the compliant sheet;
    c) sense means for detecting reflected light from said undersurface of the compliant sheet during said scanning; and
    d) processor means responsive to data derived from outputs from said sense means for determining distance values from a datum surface to portions of the compliant sheet, said distance values enabling a contour to be derived that represents said surface of said object.

12. The apparatus as recited in claim 11, wherein said support means orients said compliant sheet at an oblique angle with respect to said datum surface, and said scanning means causes said light beam to traverse along a plane parallel to said datum surface.

13. The apparatus as recited in claim 11, wherein said support means further comprises;
    an enclosed cavity that is substantially air tight; and
    means for adjusting air pressure in said enclosed cavity to support said object, while allowing said compliant sheet to form around said object.

14. The apparatus as recited in claim 11, wherein said datum surface comprises an optically transparent plate through which said light beam is projected.

15. The apparatus as recited in claim 11, wherein said undersurface of said compliant sheet includes a region with retro-reflective means affixed thereto.

16. The apparatus as recited in claim 11, wherein said undersurface of said compliant sheet includes a region with retro-reflective spheres affixed thereto.

17. The apparatus as recited in claim 11, wherein said scanning means comprises a light source and a reflective means for directing a beam of light from said reflective means in a direction that is generally orthogonal to said datum surface onto said compliant sheet.

18. The apparatus as recited in claim 11, wherein said scanning means moves a light beam evidencing multiple separate colors along said undersurface of said compliant sheet, and said sense means senses a particular color of reflected light in accordance with a distance of said compliant sheet therefrom.

19. The apparatus as recited in claim 11, wherein said object is a human foot.

20. A method of calibrating a distance measurement using a scanner and a compliant sheet, said method comprising the steps of:

a) orienting the compliant sheet along a plane with respect to a datum surface;

b) activating the scanner to scan an undersurface of the compliant sheet with a light beam;

c) sensing reflected light while scanning the undersurface of the compliant sheet;

d) computing a table which relates distance and a light value by comparing known physical distances between the regions of the compliant sheet and a datum surface, and correspondingly positioned light values measured in step c).

21. The method as recited in claim 20, comprising the further steps of:

e) placing a surface of a foot against the compliant sheet of known color so as to cause said compliant sheet to conform to a shape of the surface of the foot;

f) scanning the undersurface of the compliant sheet with said light beam;

c) sensing reflected light from said undersurface of the compliant sheet during said scanning; and d) determining distance values to portions of the compliant sheet from said table by using measured reflected light intensities to access distance values, said distance values enabling a contour to be derived of said surface of said object.

22. A method for measuring the shape of an undersurface of an object, the method comprising the steps of:

a) conforming a compliant sheet to a shape of the undersurface of said object;

b) scanning an undersurface of the compliant sheet with a beam of energy, from a vantage point that is below the compliant sheet; and c) employing reflections of said beam of energy from said compliant sheet to determine a contour of said shape of the undersurface of said object.

* * * * *